(12) United States Patent
Barthelemy et al.

(10) Patent No.: US 12,178,589 B2
(45) Date of Patent: Dec. 31, 2024

(54) SYSTEM AND METHOD FOR GENERATING A SENSORIAL STIMULUS

(71) Applicant: CYREBRO TECHNOLOGIES, Paris (FR)

(72) Inventors: Quentin Barthelemy, Lyons (FR); Louis Mayaud, Angoulême (FR)

(73) Assignee: CYREBRO TECHNOLOGIES, Paris (FR)

( * ) Notice: Subject to any disclaimer, the term of this patent is extended or adjusted under 35 U.S.C. 154(b) by 565 days.

(21) Appl. No.: 16/648,346

(22) PCT Filed: Sep. 18, 2018

(86) PCT No.: PCT/EP2018/075208
§ 371 (c)(1),
(2) Date: Mar. 18, 2020

(87) PCT Pub. No.: WO2019/053285
PCT Pub. Date: Mar. 21, 2019

(65) Prior Publication Data
US 2020/0214586 A1    Jul. 9, 2020

Related U.S. Application Data

(63) Continuation of application No. 15/707,190, filed on Sep. 18, 2017, now Pat. No. 11,154,234.

(51) Int. Cl.
*A61B 5/375* (2021.01)
*A61B 5/00* (2006.01)
(Continued)

(52) U.S. Cl.
CPC ............. *A61B 5/375* (2021.01); *A61B 5/316* (2021.01); *A61B 5/374* (2021.01); *A61B 5/377* (2021.01);
(Continued)

(58) Field of Classification Search
None
See application file for complete search history.

(56) References Cited

U.S. PATENT DOCUMENTS

| | | | |
|---|---|---|---|
| 4,846,190 A * | 7/1989 | John | A61B 5/743 600/544 |
| 2009/0030303 A1 | 1/2009 | Pradeep | |

(Continued)

FOREIGN PATENT DOCUMENTS

| | | | | |
|---|---|---|---|---|
| EP | 3143933 A1 * | 3/2017 | ........... | A61B 5/0476 |
| EP | 3 181 043 A1 | 6/2017 | | |
| WO | 2008/124566 A2 | 10/2008 | | |

OTHER PUBLICATIONS

Prasad, P. D., Halahalli, H. N., John, J. P., Majumdar, K. K. (2014). Single-trial EEG classification using logistic regression based on ensemble synchronization. IEEE Journal of Biomedical and Health Informatics, 18(3), 1074-1080. doi.org/10.1109/jbhi.2013.2289741 (Year: 2014).*

(Continued)

*Primary Examiner* — Benjamin S Melhus
*Assistant Examiner* — Samuel C Kim
(74) *Attorney, Agent, or Firm* — Maier & Maier, PLLC

(57) ABSTRACT

The present invention relates to a method for generating a sensorial stimulus using electroencephalographic data acquired from a subject, the method comprising the following steps: receiving electroencephalographic data comprising at least two electroencephalographic signals measured simultaneously from at least two electroencephalogram channels; calculating an alpha phase neuromarker on consecutive epochs of the electroencephalographic data, the alpha phase neuromarker being representative of at least the phase coherence between alpha waves recorded from the at least two electroencephalogram channels; and generating a (Continued)

sensorial stimulus representing alpha phase neuromarker using an output generator.

19 Claims, 7 Drawing Sheets

(51) Int. Cl.
| | |
|---|---|
| *A61B 5/316* | (2021.01) |
| *A61B 5/374* | (2021.01) |
| *A61B 5/377* | (2021.01) |
| *G16H 20/10* | (2018.01) |
| *G16H 20/40* | (2018.01) |
| *G16H 50/20* | (2018.01) |

(52) U.S. Cl.
CPC .......... *A61B 5/7203* (2013.01); *A61B 5/7257* (2013.01); *A61B 5/7405* (2013.01); *A61B 5/743* (2013.01); *G16H 20/10* (2018.01); *G16H 20/40* (2018.01); *G16H 50/20* (2018.01); *A61B 2505/09* (2013.01)

(56) References Cited

U.S. PATENT DOCUMENTS

| | | | |
|---|---|---|---|
| 2009/0318826 A1 | 12/2009 | Green et al. | |
| 2012/0271374 A1* | 10/2012 | Nelson | ............... A61N 1/36082 607/45 |
| 2016/0220836 A1 | 8/2016 | Parks | |
| 2017/0065199 A1 | 3/2017 | Meisel | |

OTHER PUBLICATIONS

Brunet, D., Murray, M. M., Michel, C. M. (2011). Spatiotemporal analysis of multichannel EEG: Cartool. Computational Intelligence and Neuroscience, 2011, 1-15. doi.org/10.1155/2011/813870 (Year: 2014).*

Ploner, M., Sorg, C., & Gross, J. (2017). Brain Rhythms of Pain. Trends in cognitive sciences, 21(2), 100-110. doi.org/10.1016/j.tics.2016.12.001 (Year: 2017).*

International Search Report and Written Opinion issued on Feb. 8, 2019 in corresponding International Application No. PCT/EP2018/075208; 14 pages.

Mormann, F. et al., "Mean Phase Coherence as a Measure for Phase Synchronisation and its Application to the EEG of Epilepsy Patients", Physica D, North-Holland, Amsterdam, NL, vol. 144, Jan. 1, 2000, pp. 358-369.

Newson et al., "EEG Frequency Bands in Psychiatric Disorders: A Review of Resting State Studies", Frontiers in Human Neuroscience, Newson and Thiagarajan, www.frontiersin.org., Jan. 9, 2019, vol. 12, Article 521, 24 pages.

Mayaud et al., "Alpha-Phase Synchrony EEG Training for Multi-Resistant Chronic Low Back Pain Patients: An Open-Label Pilot Study", European Spine Journal, Springer-Verlag GmbH, Part of Springer Nature, Jun. 28, 2019, vol. 28, No. 11, pp. 2487-2501.

* cited by examiner

SYSTEM AND METHOD FOR GENERATING A SENSORIAL STIMULUS

FIELD

The present invention pertains to the field of self-paced brain neuromodulation and more particularly, but not exclusively, to methods and systems for analyzing and representing neurophysiological data. In particular, the invention may be used in interactive games wherein a subject uses a neurofeedback or for the training of a subject to modify the perception of pain or reinforce self-modulation of pain pathways.

BACKGROUND

Self-paced brain neuromodulation is a training procedure that teaches self-control of brain function to a subject by measuring brain waves and providing real-time stimuli in response. During this procedure, the subject becomes aware of the changes occurring during training and will be able to assess his progress in order to achieve optimum performances. More specifically, the perceptualization of a specific brain activity allows the subject to learn to increase or decrease the said brain activity thanks to experimental psychology paradigms such as operant condition or self-regulation. There is now a long-standing evidence that a subject undergoing several neuromodulation training sessions is able to modify plasticity and generate anatomical and functional changes in the subject brain. Those modifications have also long-been associated with clinical improvement in various central nervous system conditions and chronic pain. Self-paced brain neuromodulation represents a great deal of interest especially for patients non-responding to classical clinical treatment such as medicaments, surgery or physical therapy and facing a therapeutic dead-end. The self-paced brain neuromodulation method, disclosed in the present invention, modifies a subject pain perception, also known as nociception.

The use of self-paced brain neuromodulation for the modification of subject nociception has already been suggest by John et al. (WO 2008/124566).

John et al. discloses a method for presenting a pain quantification index and a target index to perform a self-paced brain neuromodulation allowing the subject to reduce the sensation and intensity of pain. Said pain quantification index is estimated by comparison to a reference brain wave data obtained from a population normative data indicative of various reference brain wave activity (i.e. brain wave activity representative of pain absence in a subject). However, the calculation of brain activity reference is a time-consuming procedure and does not represent a reliable reference for all subject since it does not take in consideration the large variability of pathologies and therefore performances between subjects. Precisely, a subject experiencing pain is likely to exhibit changes in multiple brain areas so that the intervention is inherently non-specific.

In this context, rises the necessity to develop an easier to implement and more reliable method and system which uses a patient-specific reference.

More generally it is desirable to develop a method and a system producing self-paced brain neuromodulation for the implementation of interactive games or for pain management purpose.

The present invention discloses an improved self-paced brain neuromodulation. In the present invention, the neural activity of a subject is evaluated through the calculation of a brain activity neuromarker and the variation of said neuromarker with respect to a reference state is reported in real time to the subject in order to enable said subject to modulate its neural activity, in particular towards an improved nociception state, by self-paced neuromodulation.

SUMMARY

The present invention relates to a system for generating a sensorial stimulus using electroencephalographic data acquired from a subject, the system comprising:
  a data processing system comprising means for carrying out the following steps:
    receiving electroencephalographic data comprising at least two electroencephalographic signals measured simultaneously from at least two electroencephalogram channels;
    calculating an alpha phase neuromarker on consecutive epochs of the electroencephalographic data, representative of the phase coherence between alpha waves recorded from the at least two electroencephalogram channels and optionally alpha waves amplitude; and
  an output generator for generating a sensorial stimulus representing the numerical value of the alpha phase neuromarker.

This aspect of the present invention allows advantageously to provide to the subject a real time feedback concerning phase coherence between alpha waves recorded from different areas of his brain and optionally concerning alpha waves amplitude. This feedback allows the training of the subject for modifying nociception or in the reinforcement of self-modulation of pain pathways. This feedback may be used as well in interactive games wherein the subject uses the neuromarker feedback to modify the sensorial stimuli outputted by the system.

According to one embodiment, the system further comprises an acquisition set-up for acquiring at least two electroencephalographic signals from a subject.

According to one embodiment, the output generator comprises visual means to produce visual stimuli representing the numerical value of the alpha phase neuromarker.

According to one embodiment, the output generator comprises auditory means to produce auditory stimuli representing the numerical value of the alpha phase neuromarker.

The present invention also relates to a computer-implemented method for generating a sensorial stimulus using electroencephalographic data acquired from a subject, the method comprising the following steps:
  receiving electroencephalographic data comprising at least two electroencephalographic signals measured simultaneously from at least two electroencephalogram channels;
  calculating an alpha phase neuromarker on consecutive epochs of the electroencephalographic data representing phase coherence between alpha waves recorded from the at least two electroencephalogram channels and optionally alpha waves amplitude; and
  generating a sensorial stimulus representing alpha phase neuromarker using an output generator.

According to one embodiment, the alpha phase neuromarker is an alpha phase concentration neuromarker (APC) which concerns the phase coherence between alpha waves recorded from different areas of his brain, and the step of calculating the alpha phase concentration neuromarker comprises:

computing a Fourier transform of the at least two electroencephalographic signals on a temporal window;
averaging complex Fourier coefficients in the frequency band of alpha waves; and
calculating the alpha phase concentration neuromarker on consecutive epochs of the electroencephalographic data by computing the average over all the channels of the complex Fourier coefficients.

According to one embodiment, the alpha phase neuromarker is an alpha phase synchrony neuromarker, dependent from the amplitude and phase of the alpha waves, and the step of calculating the alpha phase synchrony neuromarker comprises:

filtering the at least two electroencephalographic signals in at least one frequency band with at least one band-pass filter, wherein one of the at least one band-pass filter filters the at least two electroencephalographic signals in the frequency band of alpha waves;
computing an average over the electroencephalographic channels obtaining an averaged signal of the at least two electroencephalographic signals; and
calculating the alpha phase synchrony neuromarker as a Frobenius squared norm a of the averaged signal on a temporal window.

According to one embodiment, the alpha phase synchrony neuromarker calculation step, is followed by a normalization step comprising:

computing a parameter p as the global field power of the averaged signal on a temporal window, wherein said temporal window corresponds to the temporal window on which is calculated the alpha phase synchrony neuromarker; and
normalizing the alpha phase synchrony neuromarker a by the global field power of the averaged signal p.

According to one embodiment, the calculation step is preceded by the step of removing the noise and/or artefact from the electroencephalographic signals.

Yet another aspect of the present invention relates to a computer program product for generating a sensorial stimulus, the computer program product comprising instructions which, when the program is executed by a computer, cause the computer to carry out the steps of the method according to any one of the embodiments described hereabove.

Yet another aspect of the present invention relates to a computer-readable storage medium comprising instructions which, when the program is executed by a computer, cause the computer to carry out the steps of the method according to any one of the embodiments described hereabove.

A first aspect of the present invention relates to a method for modifying nociception in a subject using electroencephalographic data acquired from the brain of a subject, the method comprising the following steps:

a) receiving electroencephalographic data comprising at least two electroencephalographic signals measured simultaneously from at least two electroencephalogram channels;
b) computing a Fourier transform of the at least two electroencephalographic signals on a temporal window;
c) averaging complex Fourier coefficients in the frequency band of alpha waves;
d) computing an alpha phase concentration neuromarker (APC) on consecutive epochs of the electroencephalographic data according to the formula $$APC = \left| \frac{1}{N} \sum_{n=1}^{N} e^{i\varphi_n} \right|,$$

wherein N is total number of channels in the received electroencephalographic data and $\varphi_n$ is a phase in the alpha band in the channel n; and
e) generating a sensorial stimulus representing alpha phase concentration neuromarker using an output generator.

According to one embodiment, the method for modifying nociception is a computer-implemented method.

Another feature of the present invention relates to a method for generating a first sensorial stimulus using electroencephalographic data acquired from the brain of a subject, the method comprising the following steps:

a) receiving electroencephalographic data comprising at least two electroencephalographic signals measured simultaneously from at least two electroencephalogram channels;
b) computing a Fourier transform of the at least two electroencephalographic signals on a temporal window;
c) averaging complex Fourier coefficients in the frequency band of alpha waves;
d) computing an alpha phase concentration neuromarker (APC) on consecutive epochs of the electroencephalographic data according to the formula $$APC = \left| \frac{1}{N} \sum_{n=1}^{N} e^{i\varphi_n} \right|,$$

wherein N is total number of channels in the received electroencephalographic data and $\varphi_n$ is a phase in the alpha band in the channel n; and
e) generating a first sensorial stimulus representing alpha phase concentration neuromarker using an output generator.

All the embodiments relating to the method for modifying nociception may be applied to the method for generating a first sensorial stimulus. Therefore, in the following description only the method for modifying nociception will be described in details. The "first sensorial stimulus" may be understood more generally as "sensorial stimulus" as described in the following description.

This aspect of the present invention allows advantageously to provide the subject with an instantaneous feedback concerning the phase coherence between alpha waves recorded from different areas of his brain. This feedback prompts the subject to dynamically modifying nociception reducing his clinical symptoms in a typical dose-response effect.

According to one embodiment, the step b) of the method according to the first aspect of the present invention is preceded by the step of removing the noise and/or artefact from the electroencephalographic signals.

According to one embodiment, the sensorial stimulus representing alpha phase concentration neuromarker is communicated to the subject.

According to one embodiment, the sensorial stimulus is communicated to the subject in real time.

According to one embodiment, the sensorial stimulus representation the numerical value of the alpha phase concentration neuromarker is a visual stimulus.

the sensorial stimulus representation the numerical value of the alpha phase concentration neuromarker is an auditive stimulus.

According to one embodiment, the method according to the first aspect of the present invention is controlled by a subject.

According to one embodiment, the method according to the first aspect of the present invention is supervised by a skilled physician.

According to one embodiment, the subject suffers from a chronic pain.

According to one embodiment, the subject is a cancer survivor suffering from chemotherapy-induced peripheral neuropathy.

According to one embodiment, the method according to the first aspect of the present invention is a long-term cure for the subject.

The present invention further relates to a system for modifying nociception in a subject, the system comprising:
  acquisition set-up for acquiring at least two electroencephalographic signals from a subject;
  a data processing system comprising means for carrying out the steps of the method according to the first aspect of the present invention; and
  output generator for reporting the sensorial stimulus representation the numerical value of the alpha phase concentration neuromarker.

The present invention further relates to a computer program product for modifying nociception in a subject, the computer program product comprising instructions which, when the program is executed by a computer, cause the computer to carry out the steps of the method described hereabove.

The present invention further relates to a computer-readable storage medium comprising instructions which, when the program is executed by a computer, cause the computer to carry out the steps of the method described hereabove.

A second aspect of the present invention relates to a method for training a subject to reinforce self-modulation of pain pathways using electroencephalographic data acquired from the brain of a subject, the method comprising the following steps:
  a) receiving the electroencephalographic data comprising at least two electroencephalographic signals measured simultaneously from at least two electroencephalogram channels;
  b) filtering the at least two electroencephalographic signals in at least one frequency band with at least one band-pass filter, wherein one of the at least one band-pass filter filters the at least two electroencephalographic signals in the frequency band of alpha waves;
  c) computing an average over the electroencephalographic channels obtaining an averaged signal of the at least two electroencephalographic signals;
  d) computing an alpha phase synchrony neuromarker as a Frobenius squared norm a of the averaged signal on a temporal window; and
  e) generating a sensorial stimulus representing alpha phase synchrony neuromarker using an output generator.

According to one embodiment, the method for training a subject to reinforce self-modulation of pain pathways is a computer-implemented method.

Yet another feature of the present invention relates to a method for generating a second sensorial stimulus using electroencephalographic data acquired from the brain of a subject, the method comprising the following steps:
  a) receiving the electroencephalographic data comprising at least two electroencephalographic signals measured simultaneously from at least two electroencephalogram channels;
  b) filtering the at least two electroencephalographic signals in at least one frequency band with at least one band-pass filter, wherein one of the at least one band-pass filter filters the at least two electroencephalographic signals in the frequency band of alpha waves;
  c) computing an average over the electroencephalographic channels obtaining an averaged signal of the at least two electroencephalographic signals;
  d) computing an alpha phase synchrony neuromarker as a Frobenius squared norm a of the averaged signal on a temporal window; and
  e) generating a second sensorial stimulus representing alpha phase synchrony neuromarker using an output generator.

All the embodiments relating to the method for training a subject to reinforce self-modulation of pain pathways may be applied to the method for generating a second sensorial stimulus. Therefore, in the following description only the method for training a subject to reinforce self-modulation of pain pathways will be described in details. The "second sensorial stimulus" may be understood more generally as "sensorial stimulus" as described in the following description.

This second aspect of the present invention allows advantageously to provide to the subject an instantaneous feedback concerning both amplitude of the alpha waves and phase coherence between alpha waves recorded from different areas of his brain. This feedback allows the training of the subject in the reinforcement of self-modulation of pain pathways.

According to one embodiment, the step d) of the method according to the second aspect of the present invention is followed by a normalization step comprising:
  computing a parameter p as the global field power of the averaged signal on a temporal window, wherein said temporal window corresponds to the temporal window on which is calculated the alpha phase synchrony neuromarker; and
  normalizing the alpha phase synchrony neuromarker a by the global field power of the averaged signal p.

According to one embodiment, the step c) of the method according to the second aspect of the present invention is preceded by the step of removing the noise and artefact from the electroencephalographic signal.

According to one embodiment, the sensorial stimulus representing alpha phase synchrony neuromarker is communicated to the subject.

According to one embodiment, the sensorial stimulus is communicated to the subject in real time.

According to one embodiment, the sensorial stimulus is a visual representation of the alpha phase synchrony neuromarker numerical value.

According to one embodiment, the subject is affected by a chronic pain or a cognitive-related disorder.

The present invention further relates to a system for training a subject to reinforce self-modulation of pain pathways, the system comprising:
  acquisition set-up for acquiring at least two electroencephalographic signals from a subject;

a data processing system comprising means for carrying out the steps of the method according to the second aspect of the present invention; and output generator for reporting the sensorial stimulus representation the numerical value of the alpha phase synchrony neuromarker.

The present invention further relates to a computer program product for training a subject to reinforce self-modulation of pain pathways, the computer program product comprising instructions which, when the program is executed by a computer, cause the computer to carry out the steps of the method according to the second aspect of the present invention.

The present invention further relates to a computer-readable storage medium comprising instructions which, when the program is executed by a computer, cause the computer to carry out the steps of the method according to the second aspect of the present invention.

DETAILED DESCRIPTION

Figure 1:
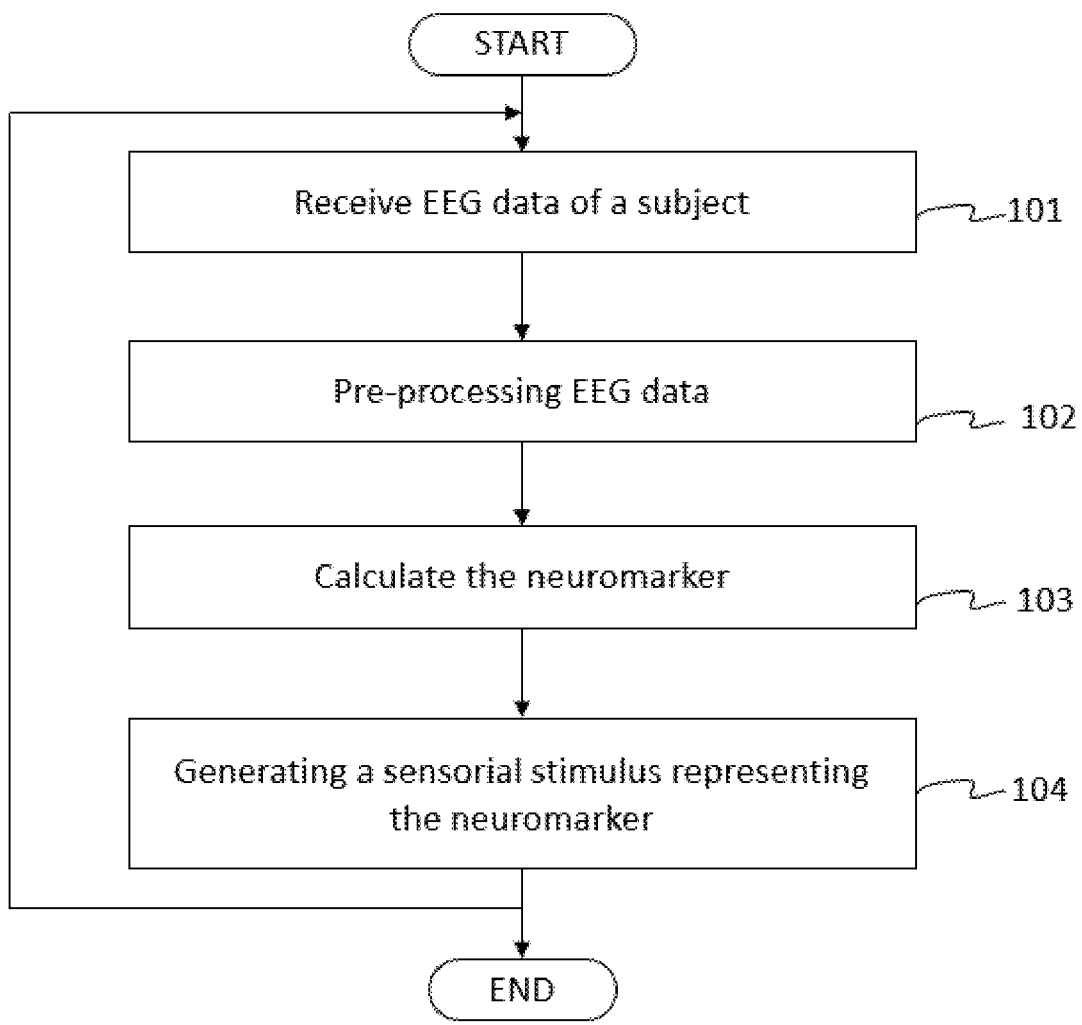
FIG. 1 shows a schematic block diagram of the self-paced neuromodulation methods in which the present invention may be embodied.

In the present invention, the following terms have the following meanings:

As used herein the singular forms "a", "an", and "the" include plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably of 5 percent.

"Computing device" refers to a computer-based system or a processor-containing system or other system that can fetch and execute the instructions of a computer program.

"Electrode" refers to a conductor used to establish electrical contact with a nonmetallic part of a circuit, preferably a subject body. For instance, EEG electrodes are small metal discs usually made of stainless steel, tin, gold, silver covered with a silver chloride coating; there are placed on the scalp at specific positions.

"Electroencephalogram" or "EEG" refers to the tracing of brain waves, by recording the electrical activity of the brain from the scalp, made by an electroencephalograph.

"Electroencephalograph" refers to an apparatus for amplifying and recording brain waves.

"Epoch" refers to a determined period or slice of neural signals.

"Global field power" refers to the spatial standard deviation, and it quantifies the amount of activity at each time point in the field considering the data from all recording electrodes simultaneously resulting in a reference-independent descriptor of the potential field.

"Real time" refers to a process for which the output is given within a time delay that is considered as smaller than the time delay required to perform the underlying task of modulation adequately. Therefore, for self-paced modulation, real time refers to a process implemented in less than 700 ms, preferably less than 500 ms, more preferably less than 400 ms, even more preferably less than 250 ms.

"Operand conditioning": refers a type of learning in which a behavior is modified by the behavior's consequences, such as reward or punishment.

"Self-paced modulation" refers to the modulation of the brain activity induced by the subject. In the sense of the present invention, self-paced modulation has the same meaning as neurofeedback and refers to the ability for the subject to control its brain electrical activity by manipulating in real-time the neuromarker. Self-paced modulation may or may not include cognitive strategy such as predefined instructions given to the subject.

"State" refers to a mental status of the subject at a particular time.

"Subject" refers to a mammal, preferably a human. In the sense of the present invention, a subject may be a patient, i.e. a person receiving medical attention, undergoing or having underwent a medical treatment, or monitored for the development of a disease.

The present invention, in some embodiments thereof, relates to neurophysiology and, more particularly, but not exclusively, to computer-implemented method and system for analyzing neurophysiological data for the purpose of modifying perception of pain, such as, but not limited to, chronic pain.

Before describing at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

It is to be understood, unless otherwise defined, that electroencephalographic signals and neural signals are both used to define signals relating to the electrical activity of neurons registered by electroencephalogram devices.

Accordingly, one or more aspects of the present disclosure relate to computer-implemented methods implementing a self-paced brain neuromodulation for modifying gating of painful stimuli. In FIG. 1, a block diagram shows the main steps included in the computer-implemented methods implemented in the present invention embodiments. The computer implemented methods of the present invention processes electroencephalographic signals and calculate neuromarker associated to the brain waves in the alpha band. Alpha waves are considered as "resting/idle state" neural oscillations in the frequency range of 7.5-12.5 Hz arising from synchronous and coherent (in phase or constructive) electrical activity of populations of neurons such as the thalamic pacemaker cells in humans. Furthermore, the synchrony of alpha waves was shown to be involved in the corticostriatal communication in a way that suggest that alpha synchrony actually modulates the nucleus accumbens (NAc) activity ("*Directed Communication between Nucleus Accumbens and Neocortex in Humans Is Differentially Supported by Synchronization in the Theta and Alpha Band*", PloS one, Horschig et al., 2015). The nucleus accumbens is a dopaminaregic area of the mesolimbic pathway that participates in the central representation of pain but also gates activity in ascending nociceptive pathways ("*The indirect pathway of the nucleus accumbens shell amplifies neuropathic pain*", Nature neuroscience, Ren et al., 2016).

More importantly, there is also a growing body of evidence ("*Involvement of the nucleus accumbens and dopamine system in chronic pain.*" Neurology, Benarroch, 2016) suggesting that the chronification of pain rewires the nucleus accumbens in way that also affects motivations and learning/reward circuitry involving dopaminergic. In the very context of chronic pain, it has long been reported experimentally that patients' nucleus accumbens activation during noxious stimulation was very different to that of a non-chronic population ("*Predicting value of pain and analgesia: nucleus accumbens response to noxious stimuli changes in the presence of chronic pain.*" Neuron, Baliki et al., 2010). More recent work on animal model even suggests that the changes affecting the nucleus accumbens in presence chronic pain are both macroscopic and molecular ("*Role of nucleus accumbens in neuropathic pain: linked multi-scale evidence in the rat transitioning to neuropathic pain.*", PAIN, Chang et al., 2014). The impact of chronic pain on the nucleus accumbens also has indirect consequence of more remote areas of the brain. For instance, the drop in motivation elicited in mice by two different models of chronic pain was proved to require a galanin receptor 1-triggered depression of excitatory synaptic transmission in indirect pathway nucleus accumbens medium spiny neurons ("*Decreased motivation during chronic pain requires long-term depression in the nucleus accumbens.*" Science, Schwartz et al., 2014). These studies not only show the importance of the nucleus accumbens in the perception and affective processing of pain but also stress the importance of lasting changes induces by chronic pain in this area as well as networks of the prefrontal cortex affecting mental health status.

According to one embodiment, the present invention comprises a preliminary step 101 of receiving the electroencephalographic signals acquired using electroencephalography from at least two electrodes, positioned onto predetermined areas of the scalp of the subject in order to obtain a multi-channel electroencephalographic signals. According to one embodiment, the electroencephalographic signals are acquired by at least 4, 8, 10, 15, 16, 17, 18, 19, 20, 21, 32, 64, 128 or 256 electrodes. According to one embodiment, the electrodes are placed on the scalp according to the 10-10 or 10-20 system, dense-array positioning or any other electrodes positioning known by the man skilled in the art. The electrodes montage may be unipolar or bipolar. In a preferred embodiment, the electrodes are placed accordingly to the 10-20 system with locations Fp1, Fp2, F7, F3, Fz, F4, F8, T3, C3, Cz, C4, T4, T5, P3, Pz, P4, T6, O1, O2, A1 and A2. In said embodiment, various types of suitable headsets or electrode systems are available for acquiring such neural signals. Examples includes, but are not limited to: Epoc headset commercially available from Emotiv, Waveguard headset commercially available from ANT Neuro, Versus headset commercially available from SenseLabs, DSI 6 headset commercially available from Wearable sensing, Xpress system commercially available from BrainProducts, Mobita system commercially available from TMSi, Porti32 system commercially available from TMSi, ActiChamp system commercially available from BrainProducts and Geodesic system commercially available from EGI. In an alternative embodiment, the electroencephalographic signals are acquired using implanted microelectrodes arrays or deep brain implants. According to one embodiment, the electrical signals arising from neural activity are acquired directly or indirectly using any cerebral imaging technique known by one skilled in the art.

The electroencephalographic signals received may be obtained with a standard recording module with sampling frequency of at least 24 Hz, preferably 32 Hz, 64 Hz, 128 Hz, 250 Hz or any other sampling frequency known by the man skilled in the art.

According to one embodiment, the electroencephalographic signals are received in real time.

According to one embodiment, the present invention further comprises a step of pre-processing of the electroencephalographic signals 102 in order to remove or reject noise. According to one embodiment, the electroencephalographic signals are further pre-processed in order to remove or reject artefact.

According to one embodiment, the electroencephalographic signals from individual scalp electrodes is digitally filtered with at least one filter chosen from group: low-frequency reject filter, high-frequency reject filter, bandpass filter, band stop filter. In a preferential embodiment, electroencephalographic signals may be filtered using first-order Butterworth band-pass filter and a third-order Butterworth notch filter; a skilled artisan would be able to select a suitable range of frequencies to reject.

One or more of the following frequency bands may be extracted by the filtering process: delta band (typically from about 1 Hz to about 4 Hz), theta band (typically from about 3 to about 8 Hz), alpha band (typically from about 7 to about 13 Hz), low beta band (typically from about 12 to about 18 Hz), beta band (typically from about 17 to about 23 Hz), and high beta band (typically from about 22 to about 30 Hz).

Higher frequency bands, such as, but not limited to, gamma band (typically from about 30 to about 80 Hz), are also contemplated.

According to one embodiment, the artefacts are corrected from the electroencephalographic signal using one or a combination of the following techniques: adaptive filtering, Wiener filtering and Bayes filtering, Hilbert-Huang Transform filter regression, blind source separation (BSS), wavelet transform method, empirical mode decomposition, nonlinear mode decomposition and the like.

One of the main source of physiological noise arises from eye movements and more precisely from eye blinks which generates large amplitude signals in the electroencephalographic signals. Those ocular artefacts present a wide spectral distribution thus perturbing all classic electroencephalographic bands, including the alpha band which is the band of interest in the method disclosed by the present invention.

In a one embodiment, the ocular artefacts are corrected using blind source separation (BSS) or regression on an electrooculogram trace.

According to one embodiment, the blind source separation for ocular artefacts removal uses Fourier co-spectral matrices as descriptors of the electroencephalographic signals, and these matrices are jointly diagonalized, providing the mixing and the separating matrices ("*On the blind source separation of human electroencephalogram by approximate joint diagonalization of second order statistics*", Clinical Neurophysiology, Congedo et al., 2008).

The neuromarker derived from the alpha brain waves are calculated 103 on these filtered electroencephalographic signals.

According to one embodiment, a sensorial stimulus representing the neuromarker derived from the alpha-band is generated by an output generator, as show in FIG. 1, step 104. According to one embodiment, said sensorial stimulus representing the alpha-derived neuromarker is further communicated to the subject. According to one embodiment, the acquisition and filtering processes according to the embodiments described hereabove are computed in real time and the sensorial stimuli are generated from the output generator in real time and communicated to the subject in real time.

One or more forms of sensory stimulation may be used including, but not limited to auditory, olfactory, tactile, somatosensory, gustatory, vestibular, or other sensory systems stimuli. In a preferred embodiment, the sensory stimulation is a visual stimulation providing a visual representation of the numerical value calculated for the alpha-derived neuromarker.

Typically, but not necessarily, the acquisition is a continuous acquisition such that electroencephalographic data are collected continuously before, during and after the generation of a stimulus.

A first aspect of the present invention relates to a self-paced neuromodulation method computer implemented for modifying nociception in a subject using electroencephalographic data acquired from the brain of a subject. In this first aspect, the nociception modification is achieved by computing and communicating to the subject an alpha-derived neuromarker value expressing the phase coherence between alpha waves recorded from different electroencephalographic channels: the alpha phase concentration neuromarker.

According to one embodiment, the at least two electroencephalographic signals, acquired and filtered as described in the embodiment above, are decomposed into their frequencies components by Fourier transform in a temporal window. Said temporal window ranging from 0.5 s to 5 s, optionally the temporal window may be of 0.5 seconds, 1 second, 1.5 seconds, 2 seconds, 2.5 seconds, 3 seconds, 3.5 seconds, 4 seconds, 4.5 seconds or 5 seconds. The signal transformation may be computed by numerical integration of a series of ordered pairs, discrete Fourier transform, or fast Fourier transform.

According to one embodiment, the Fourier transform is computed after processing the signal with a window function of about 1 s every x seconds, wherein x ranges from 0.05 s to 1 s. In a preferred embodiment, the window function is a Hamming window.

According to one embodiment, the complex Fourier coefficients are averaged in the band of alpha waves for each channel. These averaged complex coefficients may be normalized in order to have their absolute value equal to the unity.

According to one embodiment, the alpha phase concentration neuromarker (APC) is computed on consecutive epochs of the electroencephalographic data by averaging the normalized coefficients over all channels according to the formula:

$$APC = \left| \frac{1}{N} \sum_{n=1}^{N} e^{i\varphi_n} \right|,$$

wherein N is total number of channels in the received electroencephalographic data and $\varphi_n$ is a phase in the alpha band in the channel n.

According to one embodiment, a sensorial stimulus representing the value of the alpha phase concentration neuromarker is generated by an output generator.

According to one embodiment, said sensorial stimulus representing the value of the alpha phase concentration neuromarker is communicated to the subject.

A second aspect of the present disclosure relates to a self-paced neuromodulation method computer implemented for training a subject in the self-modulation reinforcement of pain pathways using electroencephalographic data acquired from the brain of a subject. In this second aspect, the alpha-derived neuromarker calculated is an alpha phase synchrony neuromarker dependent from the amplitude and phase of the alpha waves.

According to one embodiment, the at least two electroencephalographic signals, acquired as described in the embodiments above, are filtered to remove noise and artefact accordingly to the embodiment described above. According to one embodiment, the at least two electroencephalographic signals are filtered with a band-pass filter in at least one frequency band. In said embodiment, one of the at least one band-pass filter filters the at least two electroencephalographic signals in the frequency band of alpha waves.

According to one embodiment, a spatial averaging operation is computed over the electroencephalographic channels obtaining an averaged signal of the at least two electroencephalographic signals. According to one embodiment, on the spatially averaged signal is applied a moving average window of about 2 s every Δt, wherein Δt ranges from 0.05 s to 1 s.

According to one embodiment, the alpha phase synchrony neuromarker (APS) is computed as a Frobenius squared norm a of the averaged signal on a temporal window. Said temporal window ranging from 0.5 s to 5 s, optionally the temporal window may be of 0.5 seconds, 1 second, 1.5 seconds, 2 seconds, 2.5 seconds, 3 seconds, 3.5 seconds, 4 seconds, 4.5 seconds or 5 seconds.

According to one embodiment, the alpha phase synchrony neuromarker is normalized by the global field power of the averaged signal p. Said global field power is computed for the averaged signal on a temporal window, wherein said temporal window corresponds to the temporal window on which is calculated the alpha phase synchrony neuromarker. The normalized alpha phase synchrony neuromarker $APS_n$ may be obtained dividing the alpha phase synchrony neuromarker a by the global field power signal p, as p or a logarithmic normalization as follows $$APS_n = \frac{\log(1.1 + a)}{\log(1.1 + p)}$$

According to one embodiment, a sensorial stimulus representing the alpha phase synchrony neuromarker is generated by an output generator.

According to one embodiment, a sensorial stimulus representing the alpha phase synchrony neuromarker is communicated to the subject.

The electroencephalographic data can be analyzed immediately after acquisition in a real time processing or it can be recorded and stored and thereafter analyzed in a second time.

According to one embodiment, the self-paced neuromodulation methods of the present invention are beneficial for any subject experiencing pain. The subject may experience a transitory pain or chronic pain, a nociceptive pain, a neuropathic pain, a psychogenic pain, a breakthrough pain and/or a phantom pain.

In a specific embodiment, the self-paced neuromodulation methods of the present invention are especially beneficial for subject suffering from chronic pain such as chronic primary pain, chronic cancer pain, chronic posttraumatic pain, chronic headache and orofacial pain, chronic visceral pain or chronic musculoskeletal pain.

In a specific embodiment, the self-paced neuromodulation methods of the present invention are especially beneficial for subject suffering from chronic musculoskeletal pain such as lower back pain, myalgia, fibromyalgia, stress fractures, tunnel syndrome including carpal tunnel syndrome, cubital tunnel syndrome and tarsal tunnel syndrome, arthritic pain, muscle pain, repetitive strain injury, inflammations, fibrosis or tissue degradation.

In a specific embodiment, the self-paced neuromodulation methods of the present invention are especially beneficial for subject suffering from chemotherapy-induced peripheral neuropathy.

The phrase "inflammatory pain" means pain due to edema or swelling of any inflamed tissue, including inflammatory joint pain. Inflammatory joint pain includes rheumatoid arthritic pain.

The phrase "acute pain" means any pain, including, but not limited to, joint pain, osteoarthritic pain, rheumatoid arthritic pain, inflammatory pain, pain from a burn, pain from a cut, surgical pain, pain from fibromyalgia, bone cancer pain, menstrual pain, back pain, headache, static allodynia, and dynamic allodynia, that lasts from 1 minute to 91 days, 1 minute to 31 days, 1 minute to 7 days, 1 minute to 5 days, 1 minute to 3 days, 1 minute to 2 days, 1 hour to 91 days, 1 hour to 31 days, 1 hour to 7 days, 1 hour to 5 days, 1 hour to 3 days, 1 hour to 2 days, 1 hour to 24 hours, 1 hour to 12 hours, or 1 hour to 6 hours, per occurrence if left untreated. Acute pain includes, but is not limited to, joint pain, osteoarthritic pain, rheumatoid arthritic pain, inflammatory pain, pain from a burn, pain from a cut, surgical pain, pain from fibromyalgia, bone cancer pain, menstrual pain, back pain, headache, static allodynia, dynamic allodynia, acute joint pain, acute osteoarthritic pain, acute rheumatoid arthritic pain, acute inflammatory pain, acute headache, acute menstrual pain, acute back pain, and acute pain from fibromyalgia. Acute pain may be selected from acute joint pain, acute osteoarthritic pain, acute rheumatoid arthritic pain, acute inflammatory pain, acute headache, acute menstrual pain, and acute back pain. Acute pain may be selected from acute joint pain, acute osteoarthritic pain, acute rheumatoid arthritic pain, and acute inflammatory pain. Acute pain may be selected from acute joint pain, acute osteoarthritic pain, and acute rheumatoid arthritic pain. Acute pain may be selected from acute joint pain and acute osteoarthritic pain.

Further examples of disorder or conditions for which a subject would benefit from the self-paced neuromodulation methods of the present invention can be classified according to the present embodiments include, without limitation, depression, attention deficit hyperactivity disorder (ADHD), stroke, traumatic brain injury (TBI), mild TBI (commonly known as brain concussion), posttraumatic stress disorder (PTSD), epilepsy, Parkinson, multiple sclerosis, agitation, Alzheimer's disease/dementia, anxiety, panic, phobic disorder, bipolar disorder, borderline personality disorder, behavior control problems, body dysmorphic disorder, cognitive-related disorders (e.g., mild cognitive impairment), dissociative disorders, eating disorder, appetite disorder, fatigue, hiccups, impulse-control problems, irritability, mood problems, movement problems, obsessive-compulsive disorder, personality disorders, schizophrenia and other psychotic disorders, seasonal affective disorder, sexual disorders, sleep disorders, stuttering, substance abuse, Tourette's Syndrome, Trichotillomania, or violent/self-destructive behaviors.

Nevertheless, the embodiments describing the self-paced neuromodulation methods hereabove can be employed for any subject, if desired.

The invention also relates to a system for modifying nociception in a subject, the system comprising:
  acquisition set-up for acquiring at least two electroencephalographic signals from a subject;
  a data processing system comprising means for carrying out the steps of the computer-implemented method according to anyone of the embodiments described hereabove in relation with the first aspect of the invention; and
  output generator for reporting the sensorial stimulus representation the numerical value of the alpha phase concentration neuromarker.

The present invention further relates to a system to reinforce self-modulation of pain pathways in a subject, the system comprising:
  acquisition set-up for acquiring at least two electroencephalographic signals from a subject;
  a data processing system comprising means for carrying out the steps of the computer-implemented method according to anyone of the embodiments described hereabove in relation with the second aspect of the invention; and
  output generator for reporting the sensorial stimulus representation the numerical value of the alpha phase synchrony neuromarker.

Yet another aspect of the present invention relates to a system for self-paced brain neuromodulation, the system comprising:
- acquisition set-up for acquiring at least two electroencephalographic signals from a subject;
- a data processing system comprising means for carrying out the steps of the computer-implemented method for modifying nociception in a subject and the computer-implemented method to reinforce self-modulation of pain pathways in a subject according to anyone of the embodiments described hereabove; and
- output generator for reporting the sensorial stimulus representation of the numerical value of the alpha phase concentration neuromarker and/or alpha phase synchrony neuromarker.

A further aspect of the present invention relates to a system for generating a sensorial stimulation, the system comprising:
- a data processing system comprising means for carrying out the steps of the computer-implemented method a first sensorial stimulus and the computer-implemented method to a second sensorial stimulus according to anyone of the embodiments described hereabove; and
- output generator for reporting the first and/or second sensorial stimulus representation of the numerical value of the alpha phase concentration neuromarker and/or alpha phase synchrony neuromarker.

According to one embodiment, the system further comprises an acquisition set-up for acquiring at least two electroencephalographic signals from a subject. As a variant, the system may further comprise a communication module configured to allow the communication between an acquisition module configured to control measurements of an electrocardiographic signal of the subject and a remote acquisition set-up. The communication module is further configured to retrieve data and may be equipped to perform wireless data transfer.

According to one embodiment, the acquisition set-up comprises any means known by one skilled in the art enabling acquisition (i.e. capture, record and/or transmission) of electroencephalographic signals as defined in the present invention, preferably electrodes or headset as explained hereabove. According to one embodiment, the acquisition set-up comprises an amplifier unit for magnifying and/or converting the electroencephalographic signals from analog to digital format.

The present invention further relates to a computer program product for modifying nociception in a subject, the computer program product comprising instructions which, when the program is executed by a computer, cause the computer to carry out the steps of the computer-implemented method for modifying nociception according to anyone of the embodiments described hereabove in relation with the first aspect of the invention.

The present invention further relates to a computer program product to reinforce self-modulation of pain pathways in a subject, the computer program product comprising instructions which, when the program is executed by a computer, cause the computer to carry out the steps of the computer-implemented method to reinforce self-modulation of pain pathways according to anyone of the embodiments described hereabove in relation with the second aspect of the invention.

According to one embodiment, the data processing system is a dedicated circuitry or a general purpose computer, configured for receiving the data and executing the operations described in the embodiment described above. According to one embodiment, the data processing system comprises a processor and a computer program. The processor receives digitalized neural signals and processes the digitalized electroencephalographic signals under the instructions of the computer program to compute the neuromarker. According to one embodiment, the computing device comprises a network connection enabling remote implementation of the method according to the present invention. According to one embodiment, electroencephalographic signals are wirelessly communicated to the data processing device. According to one embodiment, the output generator wirelessly receives the alpha-derived neuromarker from the data processing device.

The present invention further relates to a computer-readable storage medium comprising instructions which, when the program is executed by a computer, cause the computer to carry out the steps of the computer-implemented method according to anyone of the embodiments described hereabove.

Computer programs implementing the method of the present embodiments can commonly be distributed to users on a distribution computer-readable storage medium such as, but not limited to, an SD card, an external storage device, a microchip, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

According to one embodiment, the output generator comprises any means for reporting an alpha-derived neuromarker value. According to one embodiment, the alpha-derived neuromarker value is reported using visual means, auditory means, olfactory means, tactile means (e.g. vibratory or haptic feedback) and/or gustatory means. Preferably, the alpha-derived neuromarker value is reported using a display such as lights; LEDs; a screen; a smartphone, a computer monitor or a television; or a head-mounted display.

According to one embodiment, the self-paced neuromodulation methods of the present invention are used to train self-paced neuromodulation of a subject during multiple training session. The number of training sessions may be of 5, 10, 15, 20, 25, 30, 35, 40, 45 or 50, preferably about 20. According to one embodiment, each training session consists of multiple blocks, preferably 6 blocks, each of about a few minutes, notably 5 minutes. According to one embodiment, the training sessions are made by the subject during a period of time ranging from about a few days to about a few weeks.

The reporting of the alpha-derived neuromarker value enables the perceptualization of a specific brain activity, such as nociception, allowing the subject to learn to increase or decrease said specific brain activity. According to one embodiment, the reporting of the alpha-derived neuromarker value comprises a visual reporting wherein a target, representing in real-time the alpha-derived neuromarker value of the subject, is displayed. Said target, representing the alpha-derived neuromarker value, may move along one or more directions on a display screen. The normalization of the alpha-derived neuromarker allows an easy representation of the alpha-derived neuromarker, since the values' scale of the alpha-derived neuromarker is fixed and independent from the subject.

According to an alternative embodiment, the alpha-derived neuromarker value is represented in relation to a reference state. According to this embodiment, the target representing the subject alpha-derived neuromarker value may move toward or away from a location corresponding to a representation of said reference state. The reference state may be defined as the alpha-derived neuromarker value obtained by the subject at the beginning of each training session or the alpha-derived neuromarker value obtained when the subject is doing a certain task, such as, but not limited to, reading, speaking, listening etc. Alternatively, the reference state may be defined by the alpha-derived neuromarker value obtain by the subject before the beginning of the self-paced neuromodulation training (i.e. before the first training session). The reference state may be further defined as an average alpha-derived neuromarker value obtained from a representative population not including the subject undergoing the self-paced neuromodulation training.

Figure 2:
FIG. 2 is an example of alpha-derived neuromarker value reported using visual means.

According to the embodiment wherein the alpha-derived neuromarker value is reported using visual means, an object on the screen, which position, size, color, or any other parameters can be modulated by said alpha-derived neuromarker value, is reported to the subject. For instance, it can be the representation of a plane or a hot-air balloon, whose altitude is modulated by the alpha-derived neuromarker value, as shown in FIG. 2. Said visual means may alternatively be a lights source such as but not limited to LEDs or LASERs device.

According to the embodiment wherein the alpha-derived neuromarker value is reported using auditory means, a sound, the amplitude of which is directly modulated by said alpha-derived neuromarker value, is reported to the subject. The sound can be a simple beep, water flowing, waves, rain, dongs, any kind of music, or any other sound which can be modulated in amplitude or frequency.

According to one embodiment, the improvement of the alpha-derived neuromarker value for the subject is realized through a learning process.

According to one embodiment, the learning process can be implemented according to the principles of operand conditioning. The generation of the targeted cerebral activity, improving alpha phase concentration or alpha phase synchrony can be rewarded by a positive stimulus (positive reinforcement) such as, by means of non-limiting example, diffusion of pleasant music, showing of nice images and/or an interesting video.

According to one embodiment, a deterioration of the alpha-derived neuromarker, obtained from the subject, is associated with the removal of the pleasant stimulus (negative reinforcement). Said alpha-derived neuromarker deterioration can also be associated with the communication of negative stimuli (positive punishment) such as, by means of non-limiting example, diffusion of unpleasant music, interruption of a pleasant music and/or interruption of an interesting video. According to one embodiment, the improvement of the alpha-derived neuromarker value back to a better state is rewarded by the removal of an unpleasant negative stimulation (negative punishment) and further positive reinforcement.

According to one embodiment, the learning process is implemented according to the principles of self-control by giving the subject a continuous real time representation of the alpha-derived neuromarker in order to allow said subject to gain control and modify the alpha-derived neuromarker through the desired state.

According to one embodiment, the learning process can be implemented with any other learning strategy or combination of them.

According to one embodiment, the system for biofeedback training described in patent publication EP 3 181 043 is used to promote subject learning by providing a reward to the subject; said reward being based on the difference between the alpha-derived neuromarker and a computed threshold calculated according to the computer-implemented method of said patent publication.

According to one embodiment, the self-paced neuromodulation methods of the present invention are a long-term cure for the subject.

According to one embodiment, the self-paced neuromodulation methods are controlled by a subject.

According to one embodiment, the self-paced neuromodulation methods are supervised by a skilled physician. The skilled physician may train, especially during the first session, the subject to the utilization of the methods for self-paced neuromodulation.

According to one embodiment, the self-paced neuromodulation methods are used by the subject alone. In this embodiment, the subject may use the self-paced neuromodulation methods at his residence.

The methods and the systems of the present invention may be further used to implement neurofeedback games. As the subject enters and maintains a desired brain state (i.e. monitored using alpha phase neuromarker), full control of the game controller is enabled. The subject is able to play the video game seamlessly. The game is configured to that if the subject does not maintain the desired brain state, speed and steering control of the game decrease.

In the view of the above detailed description, one skilled in the art could implement the method according to the present invention. Especially, the implementation of the method may use the following tools:

an open source toolbox for Brain-Computer Interface research such as that available on https://sccn.ucsd.edu/wiki/BCILAB;

a software platform dedicated to designing, testing and using brain-computer interfaces such as that available on http://openvibe.inria.fr/. OpenViBE platform is a software for brain-computer interface and real time neurosciences. It provides components for digital signal processing and visualization of EEG signal. It can be extended with modules in C++, Matlab and Python.

a software suite for EEG data acquisition, stimulus presentation, and brain monitoring applications such as that available on http://www.schalklab.org/research/bci2000;

While various embodiments have been described and illustrated, the detailed description is not to be construed as being limited hereto. Various modifications can be made to the embodiments by those skilled in the art without departing from the true spirit and scope of the disclosure as defined by the claims.

EXAMPLES

The present invention is further illustrated by the following examples.

Example 1—Validation of the System and Method to Reinforce Self-Modulation of Pain Pathways in a Subject The system and method for self-modulation of pain pathways proposed in the detailed description has been validated on real data.

EEG data were acquired on-line and the stimulation representing the alpha synchrony neuromarker value was communicated in real-time to the subject. The present method will be considered successful if an improvement of clinical score parameters will be observed over time from the subject.

Materials and Methods

Recordings

The electroencephalography (EEG) data was collected using a 19-channels smartBCI EEG system (Saint-Petersburg, Russia) with 19 silver-chloride electrodes fitted to a neoprene cap.

The 19 electrodes were approximately located at the extended 10-20 locations Fp1, Fp2, F7, F3, Fz, F4, F8, T3, C3, Cz, C4, T4, T5, P3, Pz, P4, T6, O1, and O2, while referenced to linked ear lobes A1 and A2. Each electrode was connected to the subject's scalp by the mean of electrolyte gel using a syringe with blunt needle. The headset was connected wirelessly to the participant laptop and interfaced with the Mensia NeuroRT Training. Mensia NeuroRT Training is a general neurofeedback software for research offering a subject database management, online eye blink removal by blind source separation techniques and artefact detection by Riemannian geometry techniques. The software allows spectral surface (sensors) and tomographic (source) neurofeedback as well as the ability to build custom neurofeedback pipeline. Mensia NeuroRT Training further comprises a custom neurofeedback pipeline according to the embodiments of the present invention which is implemented in order to reinforce alpha synchrony (upward training) as an attempt to replicate and characterize learning response and specificity of training. The effectiveness of the system of the present invention lies in the subject's ability to modulate their brain activity, either by operant conditioning or voluntary control. To that purpose, the digitized brain signals are analyzed to extract a representation of the targeted cortical area real time activity, which is translated into a visual or auditory cue. The sensory feedback constitutes the rewards mechanism that promotes learning.

Data are acquired during 20 training sessions of electro-encephalographic (EEG) alpha-synchrony neurofeedback training. Each session was composed of 6 blocks of 5 minutes, preceded by recording of 2 minutes wherein the subject keeps the eyes-open (EO) and recording of 2 minutes wherein the subject keeps the eyes-closed (EC).

Population

Patients were enrolled at a tertiary day-care clinic for physical medicine and rehabilitation after giving their informed consent about the research. Inclusion criteria comprised the presence of chronic back pain resistant any form of standard therapeutic approach including a week-long intensive multidisciplinary approach made of drug, physiotherapy, psychotherapy. The control population was recruited from participants who responded positively to the one-week intensive treatment. In order to limit heterogeneity of EEG recordings, only female participants were included in the study so as to discard known gender-related sources of EEG variability. Patients were told they could leave the research protocol at any time and without condition.

In total, 16 patients and 10 control subjects were included in the study.

Clinical Endpoints

Two types of clinical endpoints were considered for this study: electromyographic (EMG) and clinical scales, both recorded before and after the neurofeedback training, for all subjects. In addition to this, the clinical scales were taken at 6 and 12 months follow-up.

EMG Scores

EMG score is evaluated considering the median frequency of the spinal erector muscle (Dolan 1995), which is a proxy for muscular function, typically done during a hip motion with tight leg and measured:
  at right (R) versus left (L) muscles, and
  for 3 phases of the trunk flexion (forward bending starting from standing position and return):
flexion (flex), interphase flexion-extension (flex-ext) and extension (ext).

Clinical Scales

In order to assess the clinical progression of the subjects, several health questionnaires were proposed to the subject before and after the neurofeedback sessions. The health questionnaires including:
  A self-reported Body Pain visual analogous scale (EVA), from zero (no pain) to ten (maximal pain one can imagine);
  The Hospital Anxiety and Depression scale (HAD) ("*The hospital anxiety and depression scale*", Acta psychiatrica scandinavica, Zigmond, A. S. and Snaith R. P., 1983), an international self-reported scale used to assess depress or anxiety state from zero (normal) to twenty-one points for each marker; each subscale is considered clinically significant over eleven and the maximal cumulated score is forty-two; the HAD is used for its sensitivity to variations of mental state;
  The DALLAS scale ("*The Development of the Dallas Pain Questionnaire: An Assessment of the Impact of Spinal Pain on Behavior*" Spine, Lawlis et al., 1989) is a self-reported quality of life scale for patients with low back pain assessing the impact on everyday quality of life: work and leisure, anxiety, depression, and sociability; each subpart varies from zero to one hundred percent.
  The HAMILTON anxiety rating scale ("*The assessment of anxiety states by rating*", British journal of medical psychology, Hamilton, 1959) includes fourteen items (quality of sleep, muscular tension, fears, somatic symptoms in cardio-vascular and respiratory systems, neuro-vegetative, etc.) each scoring from zero to four, summing up to a maximum value of fifty-six, which is considered clinically significant above twenty; this scale is particularly useful for our patients who are suffering from multiple pain and specifically muscle pain; it also proves relevant to capture variation.

For the evolution of these clinical scores between before and after neurofeedback, a Wilcoxon signed-rank test is applied for each score on paired values. All four clinical scales were taken as well 6 months and 12 months after the end of the intervention.

Data Processing

Real Time EEG Data Processing for Training Sessions

For each block of each session:
  raw signal was band-pass filtered using a 1-45 Hz 1st-order Butterworth filter, and band-stop filtered in the frequency range 47-53 Hz with a 3rd-order Butterworth notch filter to suppress 50 Hz power line interference, filtered signal was further processed to remove signal epochs comprising ocular artefacts using a mean covariance matrix, and alpha phase synchrony neuromarker was computed across time.

Electroencephalographic signal was processed as described on-line to show to the subject a figurative representation of the alpha phase synchrony neuromarker. The processing of EEG time series in real time is an essential component of the therapeutic method described here.

Post-Hoc Analysis of Neuromarkers

In order to study the progression of the alpha phase synchrony neuromarkers across time, all subjects' recordings collected were as well stored to be processed off-line as described above. For the statistical analysis, the slopes of neuromarkers progression over training sessions and training blocks are computed for all patients with a Pearson correlation, proving a correlation coefficient R and a p-value.

In terms of learning, it is expected that a subject will gradually learn to control neuromarkers during a session (intra-session learning) and/or the changes to occur from session to sessions (inter-session), reflecting lasting effects. In order to gain a better understanding of the specificity of learning and its relation to clinical efficacy, different levels of learning were investigated:

control: to ensure that subjects did indeed acquire control of the targeted brain activity, its averaged activity within a session, that is from block to block (each TBR session is composed of 6 blocks of 5 minutes of active training) was study to reveal the presence of a trend. Showing control of the neuromarker enables subsequent learning and lasting changes;

learning: to demonstrate that subjects did learn to control the neuromarker, we looked at the improvement of its averaged value across sessions. A positive trend, would arguably relate to an increased control over the targeted brain activity and demonstrate that learning has taken place;

baseline changes: it was made herein the hypothesis that changes of baseline activity as eye open and eyes closed resting state recording taken at the beginning of each session would reflect lasting changes and re-organization the baseline brain activity.

To study these different levels of changes, the entire dataset was post-processed to extract the evolution of two pre-specified neuromarkers: the alpha phase synchrony, sensitive to both amplitude and phase which was trained and the alpha phase concentration (APC) solely sensitive to phase and arguably relating more specifically to the modulation of the nucleus accumbens, which it is believed to relate more specifically to the symptoms of chronic pain and their evolution.

Statistical Analysis

In order to demonstrate control, learning, and baseline changes, statistically significant trends had to be reliably demonstrated in the progression of EEG neuromarkers. Doing so for each individual and for many neuromarkers exposes the analysis to the risk of getting false positive (multiple-testing problem). Using a Bonferroni correction in the context of correlated variables would lead to an undesirable lack of statistical power. To circumvent this limitation, permutation statistics can be implemented where the distribution of the chosen statistics to be tested was estimated from the data permuted under the null-hypothesis. Specifically, the longitudinal time series (EO, EC, and training) for each neuromarkers (APS and APC) were permuted under the null hypothesis that the data showed no temporal monotonic trend. At each permutation the time vector was shuffle and the absolute Spearman Correlation |R| between each neuromarker and the time vector was computed. The maximum value across all neuromarkers was taken (k=6) resulting, after all permutations, in a distribution of |Rmax| statistics under the null hypothesis. Finally, the R value resulting from the real data was finally compared to the 95th percentile of that distribution to assess statistical significance. Not only this test procedure kept the probability of false positive controlled at the nominal level, but it also adjusted automatically to the degree of correlations among neuromarkers.

Finally, to assess the specificity of the statistical temporal trends identified with respect to the clinical endpoints, a correlation coefficient was computed between the slope of each neuromarker (estimated with a linear regression) and the progression in each clinical score computed as the raw difference before and after the intervention (post-pre). The statistical significance accounted for multiple correlations tests using two levels of corrections: first, the R-max method was applied to correct for the multiple clinical scores tested (k=5) and Holm-Bonferroni corrections to correct for the different neuromarkers investigated (k=2).

For the evolution of medical criteria (i.e. clinical scores and EMG data) between before and after neurofeedback, a Wilcoxon signed-rank test was applied for each score on paired values. The evolution of clinical scores before, after and at follow-ups was assessed with the same R-max permutation technique used to assess the progression of neuromarkers. All permutations were exhaustively computed (4!=24) leading to a minimum possible p-value of 0.04. Tests were one-sided.

Results

Figure 3:
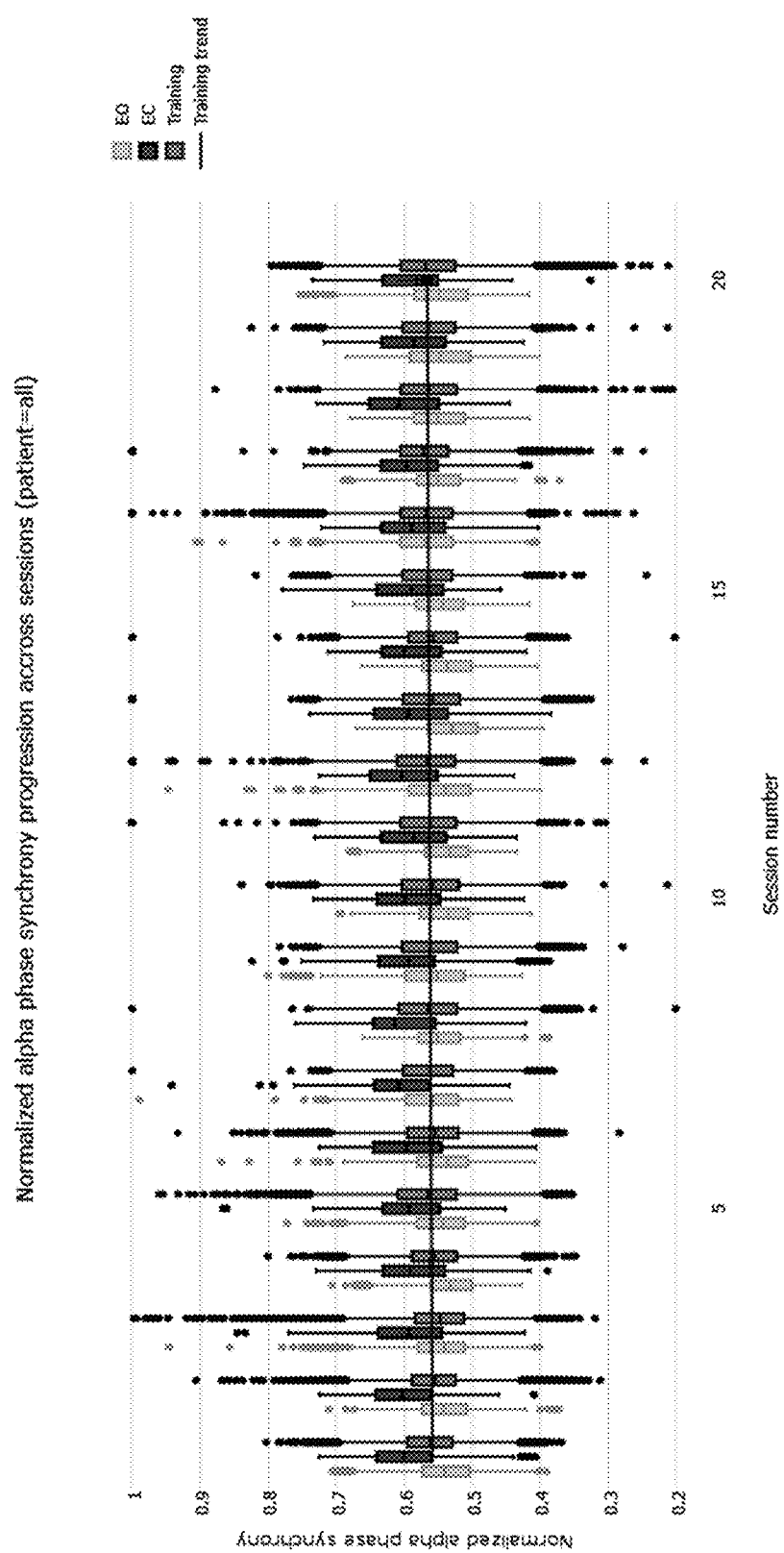
FIG. 3 is a box-plot showing the evolution through sessions of the alpha phase synchrony neuromarker when electroencephalographic signals are acquired with eyes open (EO), eyes closed (EC) or averaged across all blocks during self-paced neuromodulation training session. Training session number is represented on the x-axis and the normalized alpha phase synchrony neuromarker value is represented on the y-axis. The black line shows the positive trend of the alpha phase synchrony neuromarker over the training sessions.

FIG. 3 shows the alpha phase synchrony neuromarker evolution between session for EEG signal acquired for the subject with eyes open (EO), eyes closed (EC) and during the self-paced neuromodulation training averaged across all blocks of a session. Data acquired with eyes closed shows an elevated alpha activity as compared to the ones acquired with open eyes. Furthermore, the alpha phase synchrony neuromarker level before training shows an elevation over the eyes open recording, which possibly captures the brain activity related to the mental task proposed by the neuromodulation training. Finally, the recordings of the alpha phase synchrony neuromarker during training present a significant positive trend (p=0.0017) and a positive Pearson product-moment correlation coefficient (Pearson corr.=0.63).

Figure 4:
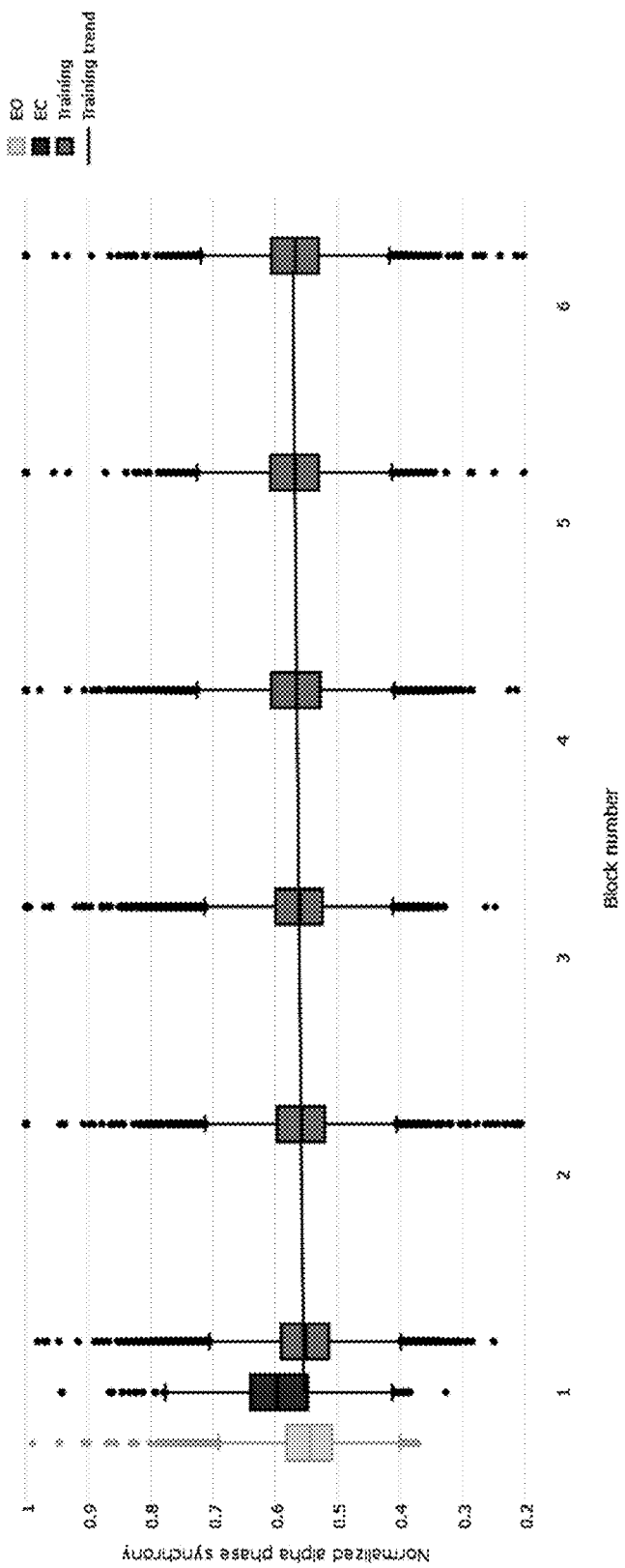
FIG. 4 is a box-plot showing intra-session alpha phase synchrony evolution averaged across all sessions when electroencephalographic signals are acquired with eyes open (EO), eyes closed (EC) or during self-paced neuromodulation training. Block number is represented on the x-axis and the normalized alpha phase synchrony value is represented on the y-axis. The line shows the positive trend over blocks.

FIG. 4 shows the interquartile evolution of the alpha phase synchrony neuromarker at rest (block 1, EEG signal acquired for the subject with eyes open EO and eyes closed EC self-paced neuromodulation before training) and during the self-paced neuromodulation training over consecutive blocks. It shows that EC recordings have an elevated alpha phase synchrony neuromarker value, which was expected due to resynchronization of visual cortex. Similarly, the recordings of the alpha phase synchrony neuromarker from block 1 to 6 present a significant positive trend (p=0.0021) and a positive Pearson product-moment correlation coefficient (Pearson corr.=0.63). This improvement over the blocks reflects changes in brain activity induced by the fact that the subject is doing the self-paced neuromodulation training task.

Figure 5:
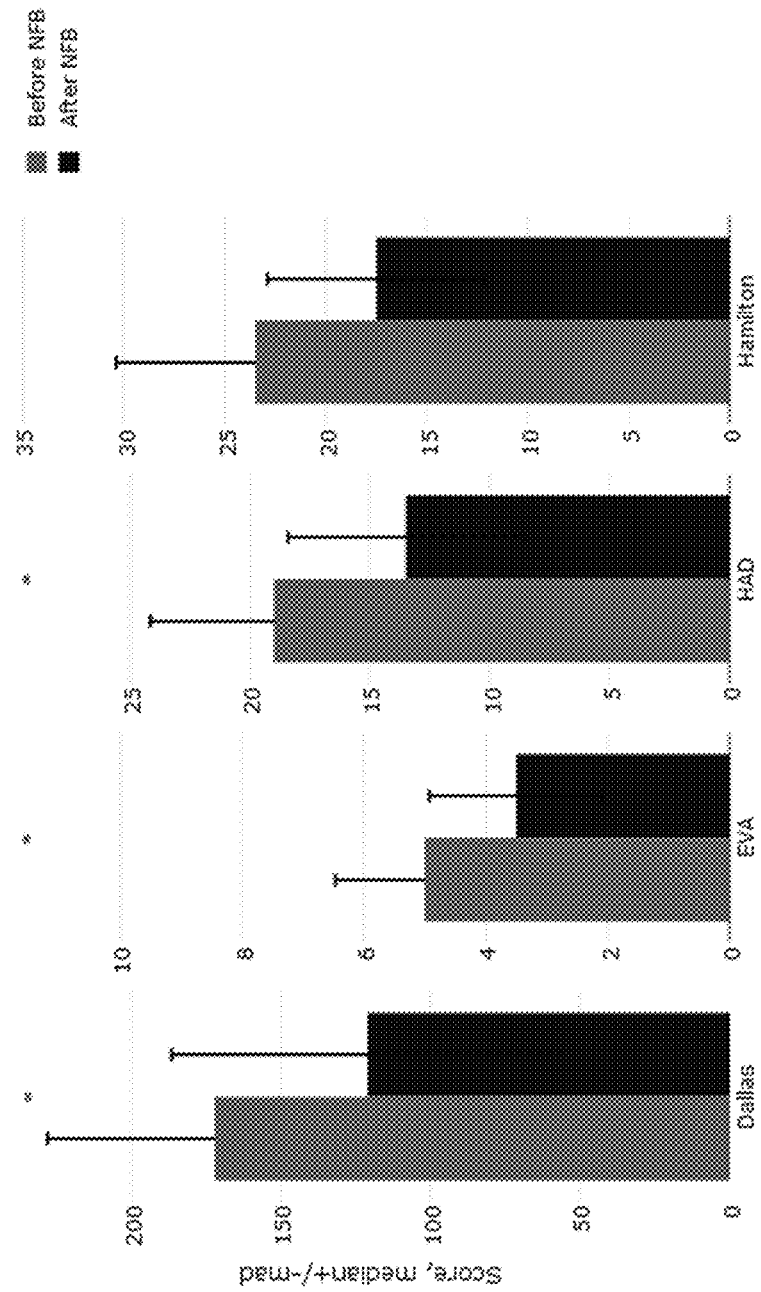
FIG. 5 is a bar plot showing the progression of clinical scores (Dallas scale, self-reported Body Pain (EVA), Anxiety and Depression scale (HAD) and Hamilton scores) averaged for the 16 patients, recorded before the self-paced neuromodulation training (gray) and after (black).

Changes in neurophysiological activity are only meaningful once associated with observed changes in symptoms. FIG. 5 shows the progression for Dallas scale, self-reported Body Pain (EVA), Anxiety and Depression scale (HAD) and Hamilton scores for the 16 patients included in the study. Median and median absolute deviation are plotted before and after the neurofeedback sessions. Clinical scores show reduction between before and after the self-paced neuromodulation training, reflecting the impact of the training.

Presence of Learning in Neuromarkers at the Group Level

Intra-session learning analysis is meant to verify that subjects were able to regulate specifically the trained neuromarker and looks at intra-session changes over blocks averaged across all patients. Each block was averaged across 20 sessions for 16 patients. The evolution of alpha phase synchrony (APS) and phase concentration (APC) at each five-minute-long training blocks showed a significant increase (permutation test: p<0.001) in the median alpha synchrony (APS) across patients from block 1 to 6. This increase reflects changes in brain activity induced by the subject doing the neurofeedback training task.

To ensure learning, the averaged activity across subject from session to session was investigated showing a statistically significant positive trend (permutation test: p=0.0006) for the neurofeedback block alpha phase synchrony (APS) neuromarker from session to session. No statistically significant trends could be found for the EO and EC condition, for any of the neuromarker (APC and APS).

Clinical Endpoints

Figure 6:
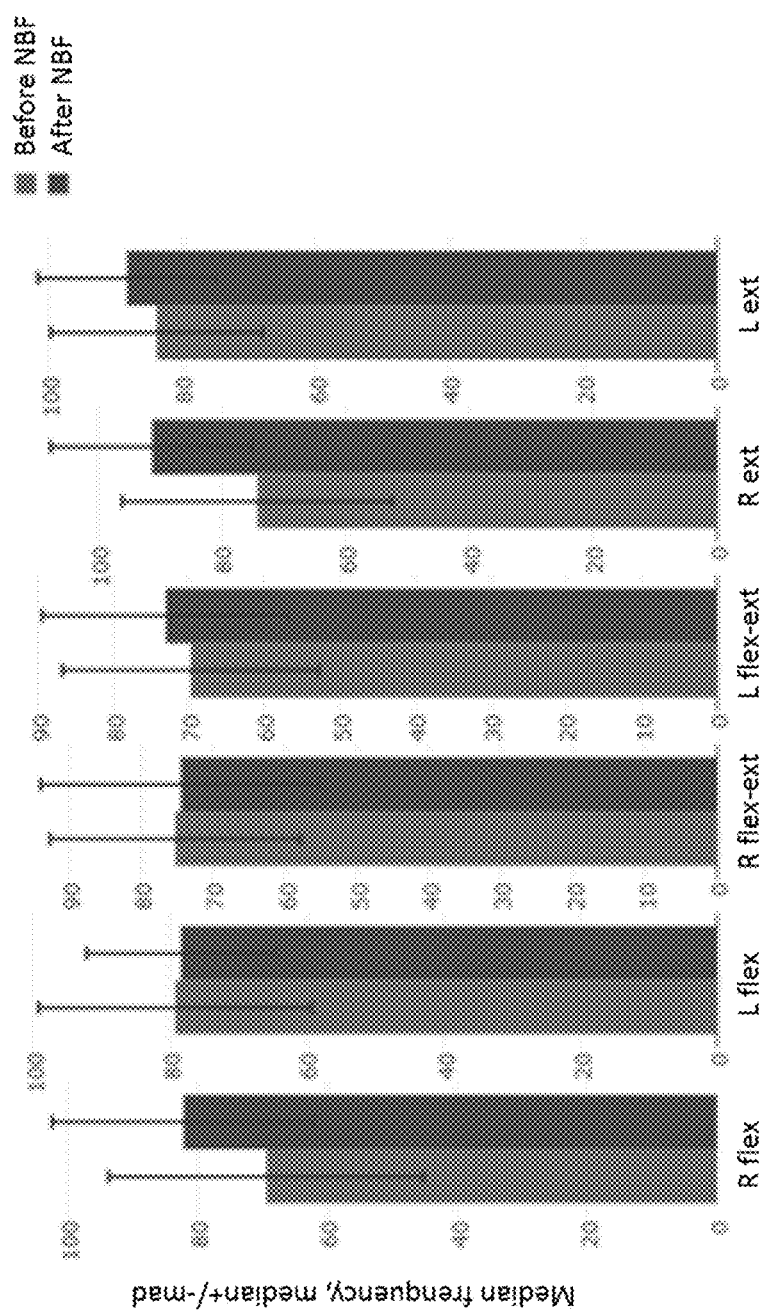
FIG. 6 shows the progression of EMG scores for 10 patients recorded before (light grey) and after (dark grey) the neurofeedback treatment for different phases of the trunk flexion: flexion of the right muscle (R flex), flexion left (L flex), interphase flexion-extension right (R flex-ext), interphase flexion-extension left (L flex-ext), extension right (R ext), extension left (L ext).

FIG. 6 shows the progression for EMG scores for only 10 of the 16 patients included in the study (the other 6 refusing to complete the EMG recording). The EMG scores, representing the median frequencies, indicates a gain in the recruitment of motor units with bigger diameters and more dynamics, the opposite of a muscular tiredness. Median and median absolute deviation are plotted before and after the neurofeedback sessions. It can be observed that the group shows an improvement of EMG scores for flexion and for extension of the right spinal erector muscle, but it is not statistically significant after correction.

Figure 7:
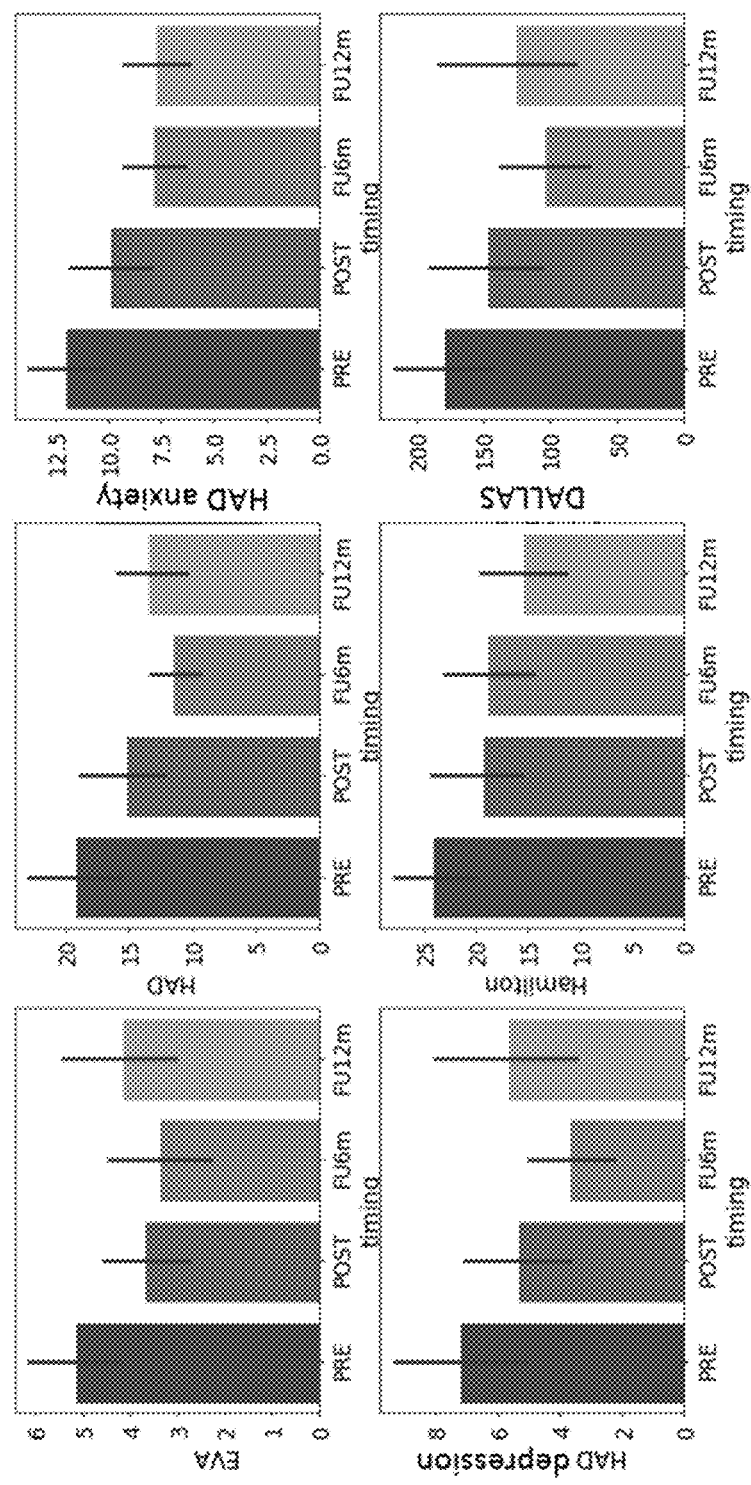
FIG. 7 shows the progression of clinical scores (Dallas, EVA, HAD total, HAD anxiety, HAD depression, and Hamilton) for the 16 patients who underwent the neurofeedback intervention, recorded before (PRE) and after (POST) the neurofeedback treatment as well as at 6 (FU6m) and 12 months (FU12m) follow-up sessions.

Changes in neurophysiological activity are only meaningful if associated with observed changes in symptoms. FIG. 7 shows the progression for Dallas, EVA, HAD and Hamilton clinical scales for the 16 patients included in the study. Median and median absolute deviation are plotted before and after the neurofeedback sessions. We can observe that the patient group shows an important reduction for each of the 4 clinical scores, and this reduction is statistically significant for the Dallas (W=20.0, corrected p=0.04) and the HAD depression (W=11.0, p=0.01). Others scores were not found statistically significant after Bonferroni correction for multiple tests: EVA (W=18.0, p=0.12) and HAD anxiety (W=28.0, p=0.16). Interestingly, the progression of the clinical scores at 6 and 12 months follow-up (also seen on FIG. 4) reveal that only the Hamilton shows of statistically significant improvement over time (R=1.0, permuted p=0.045). All other scales consistently decrease at 6 months follow-up and recover to posttreatment level after 12 months.

Finally, the alpha phase concentration neuromarker, specific to phase rather than amplitude, was found to correlate significantly with the reduction of clinical symptoms in a typical dose-response effect.

CONCLUSIONS

This pilot study validates the self-paced neuromodulation approach proposed in the present invention. According to the results, the use of alpha phase synchrony neuromarker for self-paced neuromodulation allows an effective modification of the neurophysiological activity of the subject under training. Indeed, the alpha phase synchrony neuromarker efficiently marks brain activity patterns associated to pain pathways, therefore allowing the reinforcement of self-modulation of pain pathways in a subject.

Considering the severity of the inclusion population, the reduction of severity that was observed on all clinical scales (statistically significant for the Dallas and HAD depression) seems of great clinical significance.

Data analysis first suggests that subjects have control on the targeted neuromarket (as instructed) because a positive trend was reported over the 6 five-minute-long training blocs for the APS neuromarker (R=0.95, p<0.01). The progression of alpha phase synchrony neuromarkers from session to session (R=0.63, p<0.01) suggests that subjects learn to better control, meaning that they improve their ability to activate/deactivate the associated neural population. This result should be placed in perspective with the (non-significant) reduction of the baseline EC alpha phase synchrony and the increase of the baseline EO alpha phase synchrony activity.

Over all possible combinations of neuromarkers (k=2) and available clinical endpoints (k=6), the correlation between the Dallas score and the alpha phase concentration neuromarker slope (R=−0.68) was found statistically after two rounds of correction for multiple testing (p<0.01). This result indicates very meaningfully that patients who gained control on their alpha phase concentration improved proportionally on their clinical scale.

This example reports on a pilot study offering an alpha phase synchronization personalized brain rehabilitation intervention to a population of multiresistant chronic lower back pain subjects. The intervention showed a significant and lasting response of most measured clinical scales, which is even more considering the severity of the population. It was shown first that the clinical improvement was lasting up to a year after the intervention and second that the subject did control (intrasession trends) and learned to better control (intersession trends) their alpha phase synchrony neuromarker. Third, the alpha phase concentration neuromarker was found to correlate significantly with the reduction of clinical symptoms in a typical dose-response effect. Finally, the intervention favorable safety profile and its availability as a home-use intervention makes it a potentially disruptive tool for less severe population in the context of non-steroidal anti-inflammatory drugs (NSAID) and opioid abuses.

The invention claimed is:

1. A computer-implemented method for training a subject to reinforce self-modulation of pain pathways using electroencephalographic data acquired from a brain of the subject, the method comprising the following steps:
   a) receiving the electroencephalographic data comprising at least two electroencephalographic signals measured simultaneously from at least two electroencephalogram channels;
   b) filtering the at least two electroencephalographic signals with a band-pass filter that only passes alpha waves;
   c) computing an averaged signal of the at least two filtered electroencephalographic signals;
   d) computing an alpha phase synchrony neuromarker as a Frobenius squared norm a of the averaged signal on a first temporal window; and
   e) generating a sensorial stimulus representing a numerical value of the alpha phase synchrony neuromarker, wherein said sensorial stimulus is selected from the group consisting of: visual stimulus and auditory stimulus;

f) training the subject to reinforce self-modulation of pain pathways with the generated sensorial stimulus, by reporting said sensorial stimulus to the subject using an output generator, said output generator being selected among: lights, LEDS, a screen, a smartphone, a computer monitor, a television, or a head-mounted display.

2. The computer-implemented method for training, according to claim 1, wherein computing the alpha phase synchrony neuromarker as the Frobenius squared norm a of the averaged signal on the first temporal window is followed by:
   a) computing a parameter p as a global field power of the averaged signal on a second temporal window, wherein said second temporal window corresponds to the first temporal window on; and
   b) normalizing the alpha phase synchrony neuromarker by the global field power of the averaged signal.

3. The computer-implemented method according to claim 1, wherein computing the averaged signal of the at least two filtered electroencephalographic signals, is preceded by removing noise and artefact from the at least two electroencephalographic signals.

4. The computer-implemented method according to claim 1, wherein said sensorial stimulus representing the alpha phase synchrony neuromarker is communicated to the subject.

5. The computer-implemented method according to claim 1, wherein said sensorial stimulus is communicated to the subject in real time.

6. The computer-implemented method according to claim 1, wherein, when said sensorial stimulus is the visual stimulus, the alpha phase synchrony neuromarker value is represented in relation to a reference state.

7. The computer-implemented method according to claim 6, wherein the reference state is defined as one of the following: the alpha phase synchrony neuromarker value obtained by the subject at the beginning of each training session, or the alpha phase synchrony neuromarker value obtained, when the subject is doing a certain task.

8. The computer-implemented method according to claim 6, wherein the reference state is defined as an average alpha phase synchrony neuromarker value obtained from a representative population, said representative population not including the subject who is undergoing a self-paced training session to reinforce self-modulation of pain pathways.

9. The computer-implemented method according to claim 6, wherein the reference state is defined as the alpha phase synchrony neuromarker value obtained by the subject at the beginning of a self-paced training session to reinforce self-modulation of pain pathways.

10. The computer-implemented method according to claim 1, wherein the alpha phase synchrony neuromarker value for the subject is realized through a learning process.

11. The computer-implemented method according to claim 10, wherein the learning process is implemented according to operand conditioning.

12. The computer-implemented method according to claim 11, wherein the learning process comprises rewarding the subject with a positive stimulus when the alpha phase synchrony neuromarker is improved.

13. The computer-implemented method according to claim 12, wherein the learning process further comprises punishing the subject by removing the positive stimulus when the alpha phase synchrony neuromarker is deteriorated.

14. The computer-implemented method according to claim 11, wherein the learning process comprises punishing the subject with a negative stimulus when the alpha phase synchrony neuromarker is deteriorated.

15. The computer-implemented method according to claim 14, wherein the learning process further comprises rewarding the subject by removing the negative stimulus when the alpha phase synchrony neuromarker is improved.

16. The computer-implemented method according to claim 10, wherein the learning process is implemented according to a self-control process consisting in giving the subject a continuous real time representation of the alpha phase synchrony neuromarker in order to allow said subject to gain control and modify the alpha phase synchrony neuromarker to a desired state.

17. The computer-implemented method according to claim 1, further comprising filtering the at least two electroencephalographic signals to remove ocular artefacts.

18. A system for training a subject to reinforce self-modulation of pain pathways, the system comprising:
   an acquisition set-up for acquiring at least two electroencephalographic signals from the subject;
   a data processing system for carrying out a method comprising:
   a) receiving the electroencephalographic data comprising at least two electroencephalographic signals measured simultaneously from at least two electroencephalogram channels;
   b) filtering the at least two electroencephalographic signals with a band-pass filter that only passes alpha waves;
   c) computing an averaged signal of the at least two filtered electroencephalographic signals;
   d) computing an alpha phase synchrony neuromarker as a Frobenius squared norm a of the averaged signal on a temporal window; and
   e) generating a sensorial stimulus representing the alpha phase synchrony neuromarker; and
   an output generator, by which the data processing system generates the sensorial stimulus, which reports to the subject said sensorial stimulus representing a numerical value of the alpha phase synchrony neuromarker, wherein said sensorial stimulus is selected from the group consisting of: visual stimulus and auditory stimulus, said output generator being selected among: lights, LEDS, a screen, a smartphone, a computer monitor, a television, or a head-mounted display.

19. A non-transitory computer-readable storage medium comprising instructions which, when the program is executed by a computer, cause the computer to carry out a computer-implemented method for training a subject to reinforce self-modulation of pain pathways using electroencephalographic data acquired from the brain of said subject, said method comprising:
   a) receiving the electroencephalographic data comprising at least two electroencephalographic signals measured simultaneously from at least two electroencephalogram channels;
   b) filtering the at least two electroencephalographic signals with a band-pass filter that only passes alpha waves;
   c) computing an averaged signal of the at least two filtered electroencephalographic signals;

d) computing an alpha phase synchrony neuromarker as a Frobenius squared norm a of the averaged signal on a temporal window;
e) generating a sensorial stimulus representing the alpha phase synchrony neuromarker, wherein said sensorial stimulus is selected from the group consisting of: visual stimulus and auditory stimulus; and
f) training the subject to reinforce self-modulation of pain pathways with the generated sensorial stimulus, by reporting said sensorial stimulus to the subject using an output generator, said output generator being selected among: lights, LEDS, a screen, a smartphone, a computer monitor, a television, or a head-mounted display.

\* \* \* \* \*